United States Patent

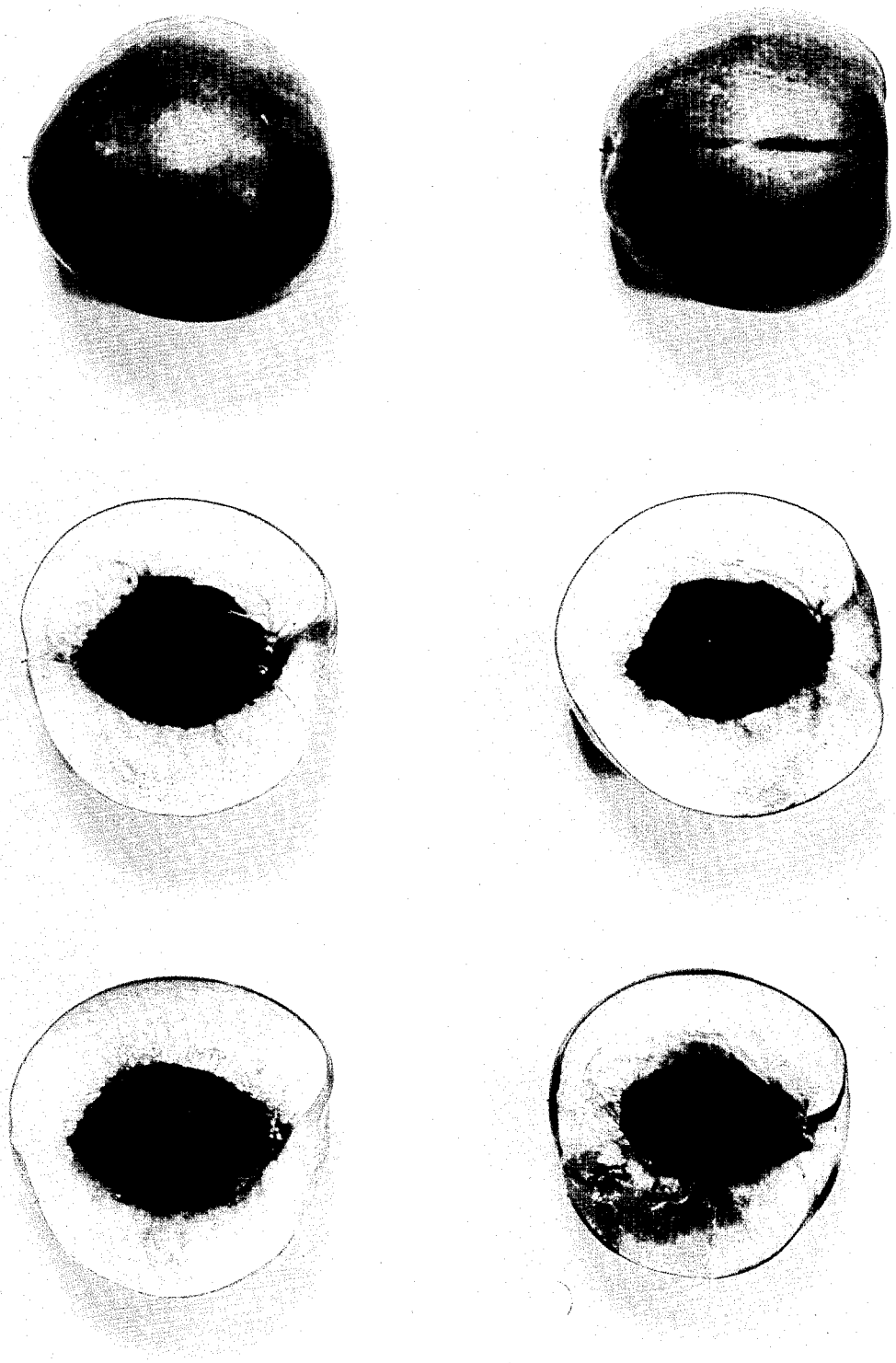

Plant Pat. 3,796

Patented Oct. 28, 1975

3,796

NECTARINE TREE

John S. Benner, 16210 E. Adams Ave., Parlier, Calif. 93648

Filed Dec. 4, 1974, Ser. No. 529,287

Int. Cl. A01h *5/03*

U.S. Cl. Plt.—41 1 Claim

ABSTRACT OF THE DISCLOSURE

A variety of nectarine tree characterized by the ripening of its yellow-fleshed fruit concurrently with that of the Gold King (U.S. Plant Pat. No. 1,424), Regal Grand (U.S. Plant Pat. No. 1,751) and Flame Kist (believed to be unpatented) nectarines from which, and all other nectarines known to ripen at the time, it is distinguished by its dominant dark red color overlaying a minutely appearing fleck-like yellow background.

BRIEF SUMMARY OF THE INVENTION

The present invention relates to a new and distinct tree of the nectarine variety and more particlarly to such a tree which produces large yellow-fleshed, globulars substantially symmetrical fruit concurrently with the Gold King (U.S. Plant Pat. No. 1,424), Regal Grand (U.S. Plant Pat. No. 1,751) and Flame Kist (unpatented) from which it is distinguished by its dominant dark red color with only minor fleck-like appearance of yellow background coloration.

Peach trees and nectarine trees have been extensively refined and improved by plant breeding and selection, as well as by the discovery and asexual reproduction of spontaneous or induced mutations or sports, natural or random breeding and the like. Such efforts have resulted in such trees producing fruit of improved flavor, increased sugar, better size, improved color, earlier ripening, later ripening, solider flesh,, improved storage and shipping characteristics, disease-resistance and other advantages.

It has long been known that bright red nectarines enjoy better sales than nectarines of other colors although otherwise of the same or equivalent quality. It has also been known that for the fresh fruit market it is desirable for nectarines to be of substantially uniform shape, to be globular and of attractive appearance, to be firm of flesh and of good flavor and to have slight or non-observable sutures. Prior to the present invention, however, no such nectarine was available during the last three weeks of August under the ecological conditions prevailing in the San Joaquin Valley of California.

ORIGIN

The nectarine tree of the present invention was discovered by the applicant during August 1972 on a farm owned by the applicant at 16210 East Adams Avenue, Parlier, Calif. as a sport in a Gold King nectarine tree (U.S. Plant Pat. No. 1,424) in an orchard thereof then being harvested. Being a long time grower of nectarines, and being alert to the desirable characteristics not available in nectarines at such harvest season, the applicant's attention was drawn to the dark red fruit produced on the sport. At the proper time, the applicant selected buds from the newly discovered sport and budded them into several host nectarine trees on his same farm and observed the growth and production of such buds during the succeeding two years. The asexual reproductions resulting from said buds were found to have the same characteristics as the sport discovered by the applicant and subsequently described.

SUMMARY

Insofar as the applicant is aware, the new variety of nectarine is most nearly similar to its parent the Gold King nectarine but bears fruit which are clearly distinguished from those of the Gold King in the following respects:

1. It is much brighter and darker red with the red enveloping virtually the entire fruits with only flecks of yellowing showing through.
2. Its flesh is solider than that of the Gold King and thus possesses better handling, shipping, and storing characteristics.
3. It has a higher sugar content while still firm thus providing a longer picking season which can be commenced somewhat earlier in relation to optimum maturity than with the fruit of the Gold King and most other nectarines.

BRIEF DESCRIPTION OF THE DRAWING

The drawing consists of a colored photograph first showing a pair of fruit of the present invention, one viewed at right angles to the suture plane and the other viewed in the suture plane followed by four halves of the nectarine of the present invention cut on the suture plane with the pits remaining in position to illustrate internal coloration.

DETAILED DESCRIPTION

For convenient reference, the botanical details of the new and distinct variety of nectarine tree are set forth in outline form with color definitions, except those in common color terms, being in accordance with the Nickerson Color Fan. It is of course to be understood that the size and shape of the trees of the subject nectarine are largely dependent upon pruning techniques, soil conditions, fertilization, and climate. The characteristics set forth are those observed under the ecological conditions prevailing in the eastern portion of the county of Fresno of the State of California. The characteristics are as follows:

Tree:

*Size.*—Medium.

*Vigor.*—Similar to Gold King.

*Productivity.*—Heavy.

*Bearing.*—Regular during limited period of observation.

*Trunk.*—Size: Dependent upon budding point, and farming techniques. Believed to be normal for nectarine trees.

*Branches.*—Branches freely.

*Leaves.*—Size: Varied widely. Length: 10 centimeters to 18 centimeters. Width: 2.5 centimeters to 5 centimeters. Shape: Lanceolate, with tip acuminate. Thickness: Medium. Margin: Markedly crenate. Color: Upper surface 5GY 4/3 and lower surface 5GY 5/6. Glandular characteristics: Irregular from none to two on each side of the petiole and/or base of the blade, occasionally more than two. Globose and approximately one millimeter in diameter. Externally green matching adjacent portions of leaf with dark centers.

Blossoms: At the same time as the Gold King with no color, size or form distinctions noted.

Fruit:

*Maturity (firm ripe).*—August 12 to August 26.

*Form.*—Substantially uniformly globular, very minute suture, symmetrical.

*Size.*—Dependent upon extent of thinning and cultural practices but when mature characteristically 5.8 to 6.2 centimeters in length, 6.0 to 6.4 centimeters in width, measured in the suture plane and 5.9 to 6.3 centimeters in thickness measured orthogonally to the suture plane.

*Base.*—Truncated.

*Pistil point.*—Very minute.

*Pit well.*—Dark red 2.5R 3/7 over red 2.5R 6/11 streaked into flesh.

*Skin.*—Thickness: Thin. Texture: Smooth. Tendency to crack: None observed. Pubescence: None. Color: Dark Red 2.5R 3/7 to red 2.5R 6/11 over yellow 2.5Y 8/12, the dark red being predominant and the yellow background appearing as minute flecks.

*Flesh.*—Amygdalin: None observed. Juice: Abundant. Texture: Firm and meaty, non-granular. Fibers: Fine and tender. Ripens: Uniformly. Flavor: Mild and sweet. Aroma: Fragrant. Eating quality: Excellent. Color: Predominantly yellow 2.5Y 9/9.

*Stone.*—Type: Cling, loosening somewhat at maturity. Fibers: Few and delicate, removed in the drawing to show stone. Size: Length 3.8 centimeters, width 2.6 centimeters, thickness 2 centimeters. Form: Obovate and cuspidate, non-symmetrical, deeply grooved. Color: Dark red 2.5R 3/7 over red 2.5R 6/11. Splitting tendency: None observed even during 1974 when many Gold King nectarine stones split.

*Use.*—Home gardens and commercial production for local markets, distant markets requiring long distance shipment, freezing, canning, drying and refrigerated storage for delayed marketing.

*Keeping quality.*—Excellent.

*Shipping quality.*—Excellent.

*Resistance to insects and disease.*—Not observed.

It is to be understood that the nectarine tree and its fruit described above may vary in response to variations in climate, soil, and cultural conditions. However, when grown with proper farming techniques under the ecological conditions prevailing in the eastern part of the county of Fresno of the State of California, its characteristics are as described above.

What is claimed is:

1. A new and distinct variety of nectarine tree substantially as herein shown and described having yellow-fleshed cling fruit characterized particularly as to novelty by ripening concurrently with its parent Gold King (U.S. Plant Pat. No. 1,424) but having a dark red skin with only minor fleck-like appearance of yellow background coloration.

No references cited.

ROBERT E. BAGWILL, Primary Examiner